US007256258B2

United States Patent
Piquet et al.

(10) Patent No.: US 7,256,258 B2
(45) Date of Patent: Aug. 14, 2007

(54) REGIOSELECTIVE LIQUID PHASE PEGYLATION

(75) Inventors: Gilles Piquet, Perosa Canavese (IT); Luca Barbero, Chivasso (IT); Silvio Traversa, Palazzo Canavese (IT); Monica Gatti, Aosta (IT)

(73) Assignee: Ares Trading S.A., Vaumarcus (CH)

( * ) Notice: Subject to any disclaimer, the term of this patent is extended or adjusted under 35 U.S.C. 154(b) by 461 days.

(21) Appl. No.: 10/398,397

(22) PCT Filed: Oct. 3, 2001

(86) PCT No.: PCT/EP01/11427

§ 371 (c)(1),
(2), (4) Date: Sep. 3, 2003

(87) PCT Pub. No.: WO02/28437

PCT Pub. Date: Apr. 11, 2002

(65) Prior Publication Data

US 2004/0176569 A1   Sep. 9, 2004

(30) Foreign Application Priority Data

Oct. 5, 2000   (EP)   ................................ 00121744

(51) Int. Cl.
*A61K 38/00* (2006.01)
(52) U.S. Cl. ..................................................... 530/335
(58) Field of Classification Search ...................... None
See application file for complete search history.

(56) References Cited

FOREIGN PATENT DOCUMENTS

WO   WO99/27897   *   6/1999
WO   WO99/27897 A1   8/1999

OTHER PUBLICATIONS

Stevenson "Characterization of Protein and Peptide sability and Solubility in Non-Aqueous Solvents" 2000, Current Pharaceutical Biotechnology, vol. 1, #2, pp. 165-182.*
Abuchowski et al., *Alteration of Immunological Properties of Bovine Serum Albumin by Covalent Attachment of Polyethylene Glycol*, J. Biol. Chem., vol. 252, No. 11, pp. 3578-3581, Jun. 10, 1977.
Abuchowski et al., *Effect of Covalent Attachment of Polyethylene Glycol on Immunogenicity and Circulating Life of Bovine Liver Catalase*, J. Biol. Chem., vol. 252, No. 11, pp. 3582-3586, Jun. 10, 1977.

R. Campbell et al., *Pegylated peptides V: Carboxy-terminal PEGylated analogs of growth hormone-releasing factor (GRF) display enhanced duration of biological activity in vivo*, J. Peptides Res., vol. 49, pp. 527-537, 1997.
G.M. Clore et al., *Solution Structure of Human Growth Hormone Releasing Factor*, J. Mol. Biol. vol. 191, pp. 553-561, 1986.
A. M. Felix et al., *Pegylated peptides IV: Enhanced biological activity of site-directed pegylated GRF analogs*, International J. of Peptide & Protein Res., vol. 46, pp. 253-264, Sep. 1995.
J. Milton Harris, *Laboratory Synthesis of Polyethylene Glycol Derivatives*, Revised Macromol. Chem. Phys., C25, pp. 325-376, 1985.
C. Monfardini et al., *A Branched Monomethoxypoly (ethylene glycol) for Protein Modification*, Bioconjugate Chem., vol. 6, pp. 62-69, 1995.
L. Sartore et al., *Enzyme Modification by MPEG with an Amino Acid or Peptide as Spacer Arms*, Applied Biochemistry and Biotechnology, vol. 27, pp. 45-54, 1991.
L. Sartore et al., *Accurate Evaluation Method of the Polymer Content in Monomethoxy (Polyethylene Glycol) Modified Proteins based on Amino Acid Analysis*, Applied Biochemistry and Biotechnology, vol. 317, pp. 213-222, 1991.
Y. Theriault et al., *Secondary Structure of the Human Growth Hormone Releasing Factor GRF 1-29) by two-dimensional $^1$H-NMR Spectroscopy*, Biopolymers, vol. 27, pp. 1897-1904, 1988.
K. Mayata et al., *Altered Properties of Serratia Superoxide Dismutase by Chemical Modification*, Agricultural Biol. Chemi., vol. 52, 6, pp. 1575-1581, 1988.
S. Zalipsky, *Chemistry of polyethylene glycol conjugates with biologically active molecules*, Advanced Drug Delivery Reviews, vol. 16, pp. 157-182, 1995.
D. A. Kloosterman et al., $^1$ *H NMR Analysis and In Vitro Bioactivity of Leu$^{27}$ -bGRF(1-29)NH$_2$ and Its D-Ala$^2$ and des-(Tyr$^1$-Ala$^2$)—Analogs*, Peptide Research, vol. 4, No. 2, pp. 72-78, 1991.
Bhattacharjya S. et al., "Effects of Organic Solvents on Protein Structures: Observation of A Structure Helical Core in Hen Egg-White Lysozyme in Aqueous Dimethylsulfoxide", *Structure, Function, Genetics*, vol. 29, pp. 492-507, (1997).
Hill, J. et al., "Three-Dimensional Solution Structure of α-Conotoxin MII By NMR Spectroscopy: Effects of Solution Environment on Helicity", *Biochemistry*, vol. 37, pp. 15621-15630, (1998).

* cited by examiner

*Primary Examiner*—Cecilia J. Tsang
*Assistant Examiner*—Roy Teller
(74) *Attorney, Agent, or Firm*—Browdy and Neimark, PLLC

(57) ABSTRACT

A method is described for a method for the regioselective liquid-phase pegylation of GRF, which increases the yield of the GRF-PEG conjugate having 1 PEG molecule covalently bound to the e-amino group of Lys$^{12}$. This method is characterized in that the reaction is carried out in a structuring solvent, such as trifluorethanol.

5 Claims, No Drawings

SEQUENCE LISTING

```
<160> NUMBER OF SEQ ID NOS: 1

<210> SEQ ID NO 1
<211> LENGTH: 29
<212> TYPE: PRT
<213> ORGANISM: Artificial
<220> FEATURE:
<223> OTHER INFORMATION: Synthetic

<400> SEQUENCE: 1

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg
            20                  25
```

REGIOSELECTIVE LIQUID PHASE PEGYLATION

FIELD OF THE INVENTION

The present invention relates to a method for the regioselective liquid-phase pegylation of GRF, which increases the yield of the GRF-PEG conjugate having 1 PEG molecule covalently bound to the ε-amino group of $Lys^{12}$. This method is characterized in that the reaction is carried out in a structuring solvent, as for example trifluorethanol.

BACKGROUND OF THE INVENTION

In the early 1980's several groups isolated and characterized growth hormone releasing factor (GRF).

GRF (also called Somatorelin) is a peptide secreted by the hypothalamus, which acts on its receptor and can promote the release of growth hormone (GH) from the anterior pituitary. It exists as 44-, 40-, or 37-amino acid peptide; the 44-amino acid form may be converted physiologically into shorter forms. All three forms are reported to be active, the activity residing mainly in the first 29 amino acid residues. A synthetic peptide corresponding to the 1-29 amino acid sequence of human GRF [GRF(1-29)], also called Sermorelin, has been prepared by recombinant DNA technology as described in European Patent EP 105 759.

Sermorelin has been used in the form of acetate for the diagnosis and treatment of growth hormone deficiency.

GRF has indeed a therapeutic value for the treatment of certain growth hormone related disorders. The use of GRF to stimulate the release of GH is a physiological method in promoting long bone growth or protein anabolism.

One problem associated with the use of GRF relates to its short biological half-life (about 12 to 30 minutes). The GRF(1-29)-$NH_2$ is subject to enzymatic degradation and is rapidly degraded in the plasma via dipeptidylpeptidase IV (DPP-IV) cleavage between residues $Ala^2$ and $Asp^3$.

It is therefore advantageous to develop biologically stable, long acting GRF analogues using specific chemical modification of GRF, in order to prevent or slow down enzymatic degradation.

Polyethylene glycol (PEG) is a hydrophilic, biocompatible and non-toxic polymer of general formula $H(OCH_2CH_2)_nOH$, wherein $n \geq 4$. Its molecular weight could vary from 200 to 20,000 Dalton.

It has been demonstrated that the chemical conjugation of PEG in its mono-methoxylated form to proteins and/or peptides significantly increases their duration of biological action. Like carbohydrate moieties in a glycoprotein, PEG provides a protective coating and increases the size of the molecule, thus reducing its metabolic degradation and its renal clearance rate.

PEG conjugation is an already established methodology for peptide and protein deivery pioneered by the fundamental studies of Davis and Abuchowski (Abuchowski et al., 1977a and 1977b). PEG conjugation to peptides or proteins generally resulted in non-specific chemical attachment of PEG to more than one amino acid residue. One of the key issues with this technology is therefore finding appropriate chemical methods to covalently conjugate PEG molecule(s) to specific amino acid residues.

Various PEG-protein conjugates were found to be protected from proteolysis and/or to have a reduced immunogenicity (Monfardini et al., 1995; and Yamsuki et al., 1988).

One approach was recently proposed for the site-specific conjugation of PEG to low molecular weight peptides, such as GRF, which was prepared by solid-phase peptide synthesis. In these conjugates a pegylated amino acid, prepared in advance, was introduced into the peptide sequence during the solid-phase synthesis. This procedure, however, dramatically complicates product purification that is known to be the critical step in solid phase synthesis. The presence of PEG, for its high molecular weight and its polydispersivity, is likely to yield final products with unacceptable impurities and/or products with missing amino acids, the latter being considered to occur commonly in the Merrifield procedure.

Mono-pegylation, meaning that only one PEG molecule is attached, using solid-phase synthesis to specific amino acid residues of $[Ala^{15}]$-GRF(1-29)-$NH_2$ has been recently reported in the literature (Felix et al., 1995). This study shows that $[Ala^{15}]$-GRF(1-29)-$NH_2$ pegylated at residues 21 or 25 retains the fill in-vitro potency of the parent $[Ala^{15}]$-GRF(1-29)-$NH_2$. There is however no in-vivo data to show whether these pegylated conjugates exhibit a longer duration of action with respect to the non-pegylated counterpart.

More recently, it has been demonstrated (Campbell et al., 1997) that the attachment of PEG with different molecular weights to the C-terminus of several analogs of GRF, again using solid-phase synthesis, had enhanced duration of action in both pig and mouse models as compared to the non-pegylated counterpart.

EP 400 472 and EP 473 084 disclose PEG derivatives obtained by using specific activated PEG derivatives. In the Examples also GRF is made to react with such activated PEG derivatives, however the specific GRF-PEG which are obtained according to such patent applications are not exactly identified nor in any way characterized. There is no mention of a specific PEG attachment site.

WO 99/27897 discloses a method for the site-specific preparation of GRF-PEG conjugates containing one or more than one PEG units (per GRF) covalently bound to $Lys^{12}$ and/or $Lys^{21}$ and/or $N^\alpha$, characterized in that the conjugation reaction between the GRF peptide and activated PEG is carried out in solution and the desired GRF-PEG conjugate is purified by chromatographic methods. According to such patent application the solvent was selected from the group consisting of a highly concentrated nicotinamide aqueous solution, a buffered aqueous solution of a defolding agent (such as urea) or a polar organic solvent selected among dimethyl sulfoxide, dimethyl formamide/buffer or acetonitrile/buffer. Dimethyl sulfoxide (DMSO) was mainly used in the Examples.

DESCRIPTION OF THE INVENTION

We have now found an improvement in the method already described in WO 99/27897, which consists in the use of a specific class of solvents, which will be herein defined as "structuring solvents". Such an improvement allows to orientate almost completely the mono-pegylation reaction towards the ε-amino group of $Lys^{12}$.

As a matter of fact, also selecting the correct molar ratio PEG/GRF, according to the present invention it is possible to obtain up to 85% of the GRF-PEG conjugate having 1 PEG molecule covalently bound to the ε-amino group of $Lys^{12}$ with respect to the total amount of mono-pegylated species. Other mono-pegylated species could have been the GRF-PEG conjugate having 1 PEG molecule covalently bound to the ε-amino group of $Lys^{21}$ the GRF-PEG conjugate conjugate having 1 PEG molecule covalently bound to the primary amino group in $N^\alpha$.

Therefore, the main embodiment of the present invention is method for the liquid-phase pegylation of GRF, which allows to obtain regioselectively GRF-PEG conjugate having 1 PEG molecule covalently bound to the ε-amino group Lys$^{12}$, characterized in that the reaction is carried out in a structuring solvent.

This and other advantages of the present process over those already described, in particular in WO 99/27897 can be listed as follows:

a single monopegylated form of GRF, in large excess with respect to the other monopegylated form(s), can be reproducibly obtained when adequate reaction conditions are applied. Selectivity of the liquid-phase PEGylation of GRF procedure has been notably improved;

a regioselective acylation reaction has been obtained without the use of protecting/deprotecting groups;

higher reaction yields are consistently observed when an excess of activated PEG is reacted with GRF. Even a three fold excess of PEG (1PEG chain per primary amine group available) does not lead to the formation of more than 10% of the poorly active in vitro dipegylated GRF form. The major species remains the monopegylated form of GRF.

According to this invention the term "GRF", unless otherwise specified, is intended to cover any human GRF peptides, with particular reference to the 1-44, 1-40, 1-29 peptides and the corresponding amides thereof (containing an amide group at the N-terminus or C-terminus). The preferred GRF peptide is GRF(1-29)-NH$_2$.

"Structuring solvents" or "structure-promoting solvents" throughout the present invention is intended to refer to those solvents or co-solvents who are able to confer stability to the predominant conformation of a peptide or protein. Generally they are organic polar solvents, such as alcohols, and are known to be used as solvents or co-solvents of peptides or proteins for NMR (Nuclear Magnetic Resonance) or CD (Circular Dichroism) studies.

Among the alcohols trifluoethanol (TFE) is preferred according to the invention.

"N$^\alpha$" throughout the present invention means the amino group at the N-terminal position of the peptide (Tyr).

The "activated PEG" (or "pegylating agent") is any PEG derivative, which can be used as protein modifier, because it contains a functional group capable of reacting with some functional group in the protein/peptide to produce the PEG-protein/peptide conjugates. A review of PEG derivatives useful as protein modifiers can be found in Harris (1985). The activated PEG can be an alkylating reagent, such as PEG aldehyde, PEG epoxide or PEG tresylate, or it can be an acylating reagent, such as PEG ester.

The activated PEG is preferably used in its mono-methoxylated form. It has preferably a molecular weight between 2,000 and 20,000. Mono-methoxylated PEG$_{5,000}$ is particularly preferred for the preparation of the activated PEG according to the present invention.

If activated PEG is an acylating agent, it preferably contains either a norleucine or ornithine residue bound to the PEG moiety via a carbamate linkage. These residues allow a precise determination of the linked PEG units per mole of peptide (see for example Sartore et al., 1991). Therefore, more in particular, the preferred activated PEG is mono-methoxylated PEG$_{5,000}$ linked by means of a carbamate bond to the alpha amino group of norleucine, that is activated at the carboxy group as succinimidyl ester.

Another preferred activated PEG can be methoxy-PEG-succinimidyl propionate ("PEG-SPA").

Branched PEGs are also in common use. The branched PEGs can be represented as R(-PEG-OH)$_m$ in which R represents a central core moiety such as pentaerythritol or glycerol, and m represents the number of branching arms. The number of branching arms (m) can range from three to a hundred or more. The hydroxyl groups are subject to chemical modification.

Another branched form, such as that described in PCT patent application WO 96/21469, has a single terminus that is subject to chemical modification. This type of PEG can be represented as (CH$_3$O-PEG-)$_p$R—X, whereby p equals 2 or 3, R represents a central core such as lysine or glycerol, and X represents a functional group such as carboxyl that is subject to chemical activation. Yet another branched form, the "pendant PEG", has reactive groups, such as carboxyl, along the PEG backbone rather than at the end of PEG chains.

All these branched PEGs can be "activated" as indicated above.

"Pegylation" is the reaction by which a PEG-protein/peptide conjugate is obtained starting from the activated PEG and the corresponding protein/peptide.

The molar ratio PEG:GRF can be 1:1, 2:1 or 3:1, but 3:1 is preferred according to the present invention.

The temperature is kept around the room temperature.

Even in this case, as for the process described in WO 99/27897, the pegylation of the present invention increases the resistance to the proteolytic degradation, does not affect, or only slightly decreases, the biological activity, depending upon the extent of pegylation and allows to obtain products (the conjugates), which are more soluble in aqueous buffered solutions.

The present invention has been described with reference to the specific embodiments, but the content of the description comprises all modifications and substitutions, which can be brought by a person skilled in the art without extending beyond the meaning and purpose of the claims.

The invention will now be described by means of the following Examples, which should not be construed as in any way limiting the present invention.

EXAMPLES

| Abbreviations | |
|---|---|
| ACN | Acetonitrile |
| DMSO | Dimethylsulfoxide |
| GRF | Growth hormone releasing factor |
| HPLC | High Performance Liquid Chromatography |
| IEX | Ion-exchange |
| mPEG-Nle-Osu | Monomethoxypoly(ethylene glycol)-norleucine succinimidyl ester |
| RP | Reverse phase |
| TEA | Triethylamine |
| TFA | Trifluoroacetic acid |
| TFE | Trifluoroethanol (2,2,2-trifluoroethanol) |

Preliminary NMR Studies on GRF

GRF is a member of a family of peptides which are known to be characterised by a predominant α-helical secondary structure, especially in presence of solvents like methanol and trifluoroethanol in aqueous solutions (see Clore et al., 1986, and Theriault et al., 1988).

Further NMR studies were more recently done at LIMA (Bioindustry Park, Ivrea, Turin, Italy). One of the main aim was to better elucidate the influence of solvents on the GRF structure, and to assess and eventual solvent-dependent conformational changes of lysine 12 and lysine 21 side-chains, changes which could modify the chemical reactivity of the amine groups.

These studies showed that GRF structure in DMSO was poorly structured and highly fluxional.

On the other hand, in the methanol/water 75% mixture, the global folding of GRF consisted of two-helix domains joined by a well-defined kink, which makes approximately a 90° angle between the axes of the -helices.

In neat trifluoroethanol, NMR studies showed a secondary structure of GRF basically α-helical at all temperature considered where the 2 α-helical tracts, are joined by a central flexible segment.

A major difference with the structure in MeOH/H$_2$O 75% mixture, is that this segment, joining the two α-helixes, exists in multiple conformations and is highly dependent upon the temperature.

Further studies made at different temperatures with TFE showed that the second-helix tract (fragment 18-28) is more stable than the first one (fragment 4-14).

The studies showed that TFE further enhances the α-helices stability already observed in methanol/water 75/25 mixture. This stabilisation appears to induce a conformational disorder in the part of the molecule (centred at fragment 16-19) joining them.

This structuring effect of TFE appears as a key element to the possible orientation of the PEGylation reaction.

This structuring effect of TFE clearly appears as a key element to the possible orientation of the PEGylation reaction.

| Materials and reagents | |
|---|---|
| Description | Lot n° |
| GRF$_{1-29}$ (Bachem) | FGRF1299603 |
| Methoxy-PEG-Nle-Osu (Shearwater Polymers) | PT-028-12 |
| Methoxy-PEG-succinimidylpropionate (SPA), (Fluka) | 85969 |
| Trifluoroethanol (TFE), (Aldrich), spectrophotometric grade | |

General Method of Synthesis

To GRF$_{1-29}$ bulk powder is added at once to trifluoroethanol. Dissolution rapidly occurs at room temperature under gentle agitation up to [GRF]=20 mg/ml in trifluoroethanol (TFE).

The chosen activated PEG reagent is then added under stirring at once as a dry powder, or in TFE solution, to reach final PEG:GRF molar ratios of 1:1, 2:1, or 3:1 (3:1 ratio is the preferred one).

The reaction mixture is then stirred at room temperature for a minimum of 6 hours. Trifluoroethanol is then evaporated under vacuum (30° C. water bath, 60 mTorr vacuum) and the reaction mixture stored at −80° C. before purification.

Results

The quenched reaction mixture of GRF, monopegylated, and dipegylated species, is analyzed by reverse-phase HPLC and the respective yield of each species determined in percentage of area. The respective ratio of the two monopegylated species at Lysine 12 and Lysine 21 is determined after purification of the crude material and in process analysis by reverse-phase HPLC.

Table 1 shows the results obtained at different molar ratio of PEG and GRF in DMSO and TFE.

TABLE 1

PEGylation of GRF reaction yields and ratio.

| | in DMSO | | | in TFE | | |
|---|---|---|---|---|---|---|
| PEG:GRF Molar ratio | 1:1 | 1.5:1 | 2:1 | 1:1 | 2:1 | 3:1 |
| Reaction time (h) | 3  22 | 3 | 3 | 3  22 | 22 | 6 |
| GRF unreacted (%*) | 32  33 | 19 | 4 | 70  58 | 35 | 26 |
| GRF-1PEG (%*) | 48  48 | 51 | 20 | 25  37 | 53 | 65 |
| GRF-2PEG (%*) | 20  19 | 30 | 74 | 5  5 | 12 | 9 |
| GRF-1PEG-Lys$^{12}$ (%$^a$) | 50 | 47 | 48 | 96  96 | 96 | 96 |

%*means weight percentage in the final reaction product
%$^a$means weight percentage of GRF-1PEG-Lys$^{12}$ with respect to the total amount GRF-1PEG-Lys$^{12}$ + GRF-1PEG-Lys$^{21}$.
"GRF-1PEG" refers to the total amount of mono-pegylated species
"GRF-2PEG" refers to the total amount of di-pegylated species Comments to the Results of Table 1

A maximum yield of 51% of GRF-1PEG-5K has been obtained in presence of DMSO, yield which dramatically decrease (from 51 to 20%) in a two-fold excess of PEG. On the contrary and quite unexpectedly, a two-fold excess of PEG versus GRF in presence of ThE increases the yield of GRF-1PEG. The same observation can be made with a three-fold excess of PEG.

This example constitutes one of the main differences between the processes in DMSO and TFE. The reaction in TFE proceeds in a regioselective manner towards the quasi-exclusive formation of the pegylated GRF in position 12.

Table 2 indicates the ratio in % area obtained in RP-HPLC of the various species of the reaction mixture in two solvents, dimethylsulfoxide and trifluoroethanol, at various ratios, and with two different activated PEG with the same reactive succinimidyl ester (see FIG. 1).

TABLE 2

Comparison yields and ratio of the various species obtained during PEGylation of GRF in DMSO and TFE solution.

| | in DMSO | | In TFE | | | | |
|---|---|---|---|---|---|---|---|
| | PEG-Nle | PEG-SPA | PEG-Nle | PEG-SPA | PEG-SPA | PEG-Nle | PEG-SPA |
| PEG:GRF Molar ratio | 1:1 | 1:1 | 1:1 | 1.1 | 2:1 | 3:1 | 4:1 |
| Reaction time (h) | 3 | 3 | 24 | 24 | 24 | 24 | 24 |

TABLE 2-continued

Comparison yields and ratio of the various species obtained during PEGylation of GRF in DMSO and TFE solution.

| | in DMSO | | In TFE | | | | |
|---|---|---|---|---|---|---|---|
| | PEG-Nle | PEG-SPA | PEG-Nle | PEG-SPA | PEG-SPA | PEG-Nle | PEG-SPA |
| GRF unreacted (%*) | 32 | 31 | 53.9 | 51 | 34.6 | 26.2 | 5.5 |
| GRF-1PEG (%*) | 48 | 48.9 | 43.6 | 45 | 57 | 65 | 64 |
| GRF-2PEG (%*) | 18 | 16 | 2.5 | 3.3 | 8.6 | 8.6 | 30.1 |
| GRF-1PEG-Lys$^{12}$ (%$^b$) | 45 | 45 | 75 | 79 | 80 | 82.7 | 85 |

%*means weight percentage in the final reaction product
%$^b$means weight percentage of GRF-1PEG-Lys$^{12}$ with respect to the total amount monopegylated GRF forms.

Comments to the Results of Table 2

Comparable results are obtained with either activated PEG. The reaction in absence of TEA, proceed with a different selectivity in TFE. In presence of a three to 4-fold excess of PEG, 50% of GRF-1PEG-Lys$^{12}$ species is formed, twice as much as the maximum amount obtained in DMSO. The results obtained with a PEG:GRF ratio are the best results obtained under the conditions tested.

CONCLUSIONS

PEGylation of GRF process in TFE lead to the formation of a major species, the GRF-1PEG-Lys$^{12}$. The use of TFE as solvent reaction was showed to increase the selectivity of the pegylation. TEA as nucleophilic enhancer orientates the positioning of the PEG chains onto the GRF peptide.

Supported by the structuring effect of TFE on GRF$_{1-29}$ amide (NMR data), possible advantages of this process over the process in DMSO are numerous and can be summarized as follow:
  a regioselective acylation reaction has been obtained without the use of protecting/deprotecting groups;
  higher yields of monopegylated GRF were experimentally obtained in presence of TFE, with respect to the reaction in DMSO;
  a large scale production of the monopegylated form of GRF will benefit of the advantages described within this protocol.

REFERENCES

Abuchowski A. et al., *J. Biol. Chem.*, 252, 3571-3581, 1977a;
Abuchowsli A. et al., *J. Biol. Chem.*, 252, 3582-3586, 1977b;
Campbell R. et al. *J. Peptide Res.*, 49, 527-537, 1997;
Clore G. M. et al., *J. Mol. Biol.*, 191, 553-561 (1986).
Felix A. M. et al., *Int. J. Peptide Protein Res.*, 46, 253-264, 1995;
Harris J. M., *Rev. Macromol. Chem. Phys.*, C25, pp. 325-76, 1985;
Monfardini et al., *Biocon. Chem.*, 6, 62-69, 1995;
Sartore L. et al., *Appl. Biochem. Biotechnzol.*, 27, 45, 1991;
Sartore L., et al., *Applied Biochem. Biotechnol.*, 31, 213-22, 1991;
Theriault Y. et al., *Biopolymers*, 27, 1897-1904, 1988;
Yamsuki et al., *Agric. Biol. Chem.*, 52, 2185-2196, 1988;
Zalipsky S. et al., *Advanced Drug Delivery Reviews*, 16, 157-182, 1995.

The invention claimed is:

1. A method for the liquid-phase regioselective synthesis of a GRF-PEG conjugate having one PEG unit covalently bound to the ε amino group of Lys$^{12}$, comprising conjugating the GRF peptide and an activated PEG in a structuring solvent consisting of trifluoroethanol.

2. The method of claim 1, wherein the GRE peptide is h-GRF(1-29)-NH$_2$.

3. The method of claim 1 or 2, wherein the activated PEG is an alkylating or acylating PEG in its mono-methoxylated form.

4. The method of claim 1 or 2, in which the conjugation reaction is carried out at room temperature.

5. The method of claim 3, in which the conjugation reaction is carried out at room temperature.

* * * * *